US00PP26918P3

(12) United States Plant Patent
Zaiger et al.

(10) Patent No.: US PP26,918 P3
(45) Date of Patent: Jul. 12, 2016

(54) INTERSPECIFIC TREE NAMED 'MALIBU'

(50) Latin Name: ***Interspecific Prunus* species**
Varietal Denomination: Malibu

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 86 days.

(21) Appl. No.: 14/544,120

(22) Filed: Nov. 26, 2014

(65) Prior Publication Data

US 2016/0150699 P1 May 26, 2016

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Susan McCormick Ewoldt

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, semi-spreading growth habit.
2. Tree having a heavy and regular production of fruit.
3. Fruit with an attractive orange/yellow skin color.
4. Fruit having a good balance between acid and sugar with an average Brix of 17.0°.
5. Fruit with good handling and shipping qualities.

1 Drawing Sheet

Botanical designation:
Interspecific *Prunus* species.
Variety denomination: 'Malibu'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Cot-N-Candy' Interspecific (U.S. Plant Pat. No. 17,827), 'Escort' Interspecific (U.S. Plant Pat. No. 18,537) and the proprietary non-patented interspecific selection '42ZC692'.

STATEMENT REGARDING FEDERALLY SPONSORED RESEARCH AND DEVELOPMENT

Not applicable.

ORIGIN OF THE VARIETY

The new variety of interspecific tree, a combination of crosses between (*Prunus armeniaca* and *Prunus salicina*)

was originated by us in our experimental orchard located near Modesto, Calif. from an open pollinated non-patented interspecific seedling selection with the field identification number '42ZC692'. The seed parent (42ZC692) originated from an open pollinated seedling selection from 'Cot-N-Candy' Interspecific (U.S. Plant Pat. No. 17,827). A large number of these open pollinated seedlings were budded on established trees of 'Nemaguard' Rootstock (non-patented) to enhance earlier fruit production and under close and careful observation the present seedling exhibited desirable fruit and tree characteristics and was selected in 2003 for additional asexual propagation and commercialization.

ASEXUAL REPRODUCTION OF THE VARIETY

In 2003 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present variety of interspecific tree [Apricot×((Plum×Plumcot)×Plumcot)×Apricot]×[unknown pollen] is of medium size, vigorous, semi-spreading growth and a regular and productive bearer of medium size, orange/yellow flesh, freestone fruit with a good balance between acid and sugar and very good flavor and eating quality. The fruit is further characterized by having an attractive orange/yellow skin color with good handling and storage quality. In comparison to its non-patented interspecific seed parent (42ZC692) the fruit of the new variety has a higher degree of Brix of 17.0° compared to 14.6° and is approximately 7 days earlier in maturity. In comparison to its ancestor 'Cot-N-Candy' Interspecific (U.S. Plant Pat. No. 17,827) the fruit of the new variety has orange/yellow flesh compared to white. In comparison to the commercial variety 'Escort' Interspecific (U.S. Plant Pat. No. 18,537) the fruit of the new variety has improved flavor and eating quality and is approximately 6 days later in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 7 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 7 year old specimens grown near Modesto, Calif., with color in accordance with Munsell Book of Color published in 1958.

Tree:

*Size.*—Medium to large, usually pruned to 3 to 3.5 meters in height and width for economical harvesting of fruit. Size varies with different cultural practices.

*Vigor.*—Vigorous, growth of 1.5 to 2 meters in height the first growing season. Varies with soil type, fertility of soil and cultural practices.

*Form.*—Semi-spreading, usually pruned to vase shape.

*Branching habit.*—Semi-spreading, crotch angle approximately 35°, increases with heavy crop load.

*Productivity.*—Productive, thinning and spacing of fruit necessary for desired market size. Fruit set varies with climatic conditions during bloom time.

*Bearer.*—Regular, adequate fruit set 5 consecutive years. No alternate bearing observed.

*Fertility.*—Self-fertile, sets fruit under bag.

*Density.*—Medium dense, usually pruned to vase shape to allow more sunlight to center of tree to enhance fruit color and health of fruit spurs.

*Hardiness.*—Hardy in all stone fruit growing areas of California. Tree grown in USDA Hardiness Zone 9. Winter chilling requirement approximately 800 hours at or below 45° F.

Trunk:

*Size.*—Large. Average circumference 58.4 cm at 20.2 cm above ground on a 7 year old tree.

*Stocky.*—Medium stocky.

*Texture.*—Medium shaggy, roughness increases with age.

*Color.*—Varies from 7.5YR 2/2 to 10YR 4/2.

Branches:

*Size.*—Medium to large. Average circumference 30.5 cm at 1.2 meters above ground. Crotch angle approximately 35°, increases with heavy crop load.

*Surface texture.*—New growth relatively smooth. Mature growth medium rough, roughness increases with age.

*Lenticels.*—Average number 31 in a 25.8 sq cm area. Average length 2.8 mm. Average width 1.7 mm. Color varies from 2.5Y 8/4 to 2.5Y 7/4.

*Color.*—New growth varies from 2.5YR 3/4 to 5GY 4/6. Mature growth varies from 5YR 3/2 to 7.5YR 2/2, varies with age of growth.

Leaves:

*Size.*—Large. Average length 94.0 mm. Average width 80.1 mm.

*Form.*—Ovate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins. Lower surface relatively smooth, except for small ridges created by midrib and pinnate venation. Both upper and lower surfaces glabrous.

*Petiole.*—Average length 32.6 mm. Average width 1.8 mm. Longitudinally grooved. Surface — very finely pubescent. Color varies from 7.5R 4/8 to 7.5R 3/8.

*Glands.*—Type — globose. Size — small. Average length 0.8 mm. Average diameter 0.7 mm. Average number 2, varies from 1 to 4. Located primarily on the upper portion of the petiole and base of leaf blade. Color varies from 7.5R 3/6 to 7.5R 2/8.

*Stipules.*—None present at the time of measurement.

*Color.*—Upper surface varies from 5GY 3/6 to 7.5GY 4/4. Lower surface varies from 5GY 5/4 to 7.5GY 5/4. Midvein color varies from 2.5GY 9/2 to 7.5R 4/8.

Flower buds:

*Size.*—Medium to large. Average length 15.4 mm. Average diameter 10.0 mm.

*Hardiness.*—Hardy with respect to California winters.

*Density.*—Dense.

*Form.*—Conical, becoming elongated just before opening.

*Pedicel.*—Average length 2.0 mm. Average width 1.6 mm. Color varies from 2.5GY 6/6 to 5GY 6/6. Surface glabrous.

*Color.*—Varies from 7.5RP 6/12 to N 9.5/ (white).

*Number of buds per spur.*—Varies from 7 to 14, average number 11. Varies with age of spur.

Flowers:

*Blooming period.*—Date of First Bloom Feb. 21, 2014. Date of Petal Fall Mar. 2, 2014, varies slightly with climatic conditions.

*Size.*—Medium to large. Average height 19.1 mm. Average diameter 25.2 mm.

*Petals.*—Normally 5, alternately arranged to sepals. Size — medium to large. Average length 14.7 mm. Average width 15.0 mm. Shape — orbicular. Arrangement — overlapping. Margin — sinuate. Petal apex — rounded. Petal base — rounded to somewhat truncated. Color varies from 5RP 9/2 to N 9.5/ (white), fades with age of flower. Both upper and lower surfaces glabrous.

*Sepals.*—Normally 5, alternately arranged to petals. Size — large. Average length 6.3 mm. Average width 5.3 mm. Shape — ovate. Margin — entire. Apex rounded to triangular. Both upper and lower surfaces glabrous. Color — upper surface varies from 2.5R 3/6 to 2.5R 3/8. Lower surface varies from 2.5R 3/8 to 5R 3/10.

*Stamens.*—Average number per flower 37. Average filament length 11.6 mm. On average, the stamens are above the height of the petals. Filament color N 9.5/ (white). Anther color varies from 5Y 8/8 to 5Y 8/10.

*Pollen.*—Self-fertile, fruit set while under bag. Color varies from 5Y 7/8 to 5Y 7/10.

*Pistil.*—Number — normally one. Surface — pubescent. Average length 17.1 mm. Position of stigma even with anthers. Color varies from 7.5Y 8.5/4 to 10Y 8.5/4.

*Fragrance.*—Heavy.

*Color.*—Varies from 5RP 9/2 to N 9.5/ (white). Varies with age of flower.

*Number flowers per flower bud.*—Average 3, varies from 2 to 4.

*Pedicel.*—Average length 2.3 mm. Average width 1.9 mm. Color varies from 2.5GY 6/6 to 5GY 6/6. Surface glabrous.

Fruit:

*Maturity when described.*—Firm ripe and ready for consumption.

*Date of first picking.*—Jun. 8, 2014.

*Date of last picking.*—Jun. 18, 2014, varies slightly with climatic conditions.

*Size.*—Medium. Average diameter axially 53.2 mm. Average transversely in suture plane 54.8 mm. Average across the suture plane 53.7 mm. Average weight 88.0 grams, varies slightly with fertility of the soil, amount of thinning and climatic conditions.

*Form.*—Globose to slightly elongated.

*Suture.*—Slightly lipped.

*Ventral surface.*—Slightly lipped.

*Apex.*—Slightly retuse.

*Base.*—Retuse.

*Stem cavity.*—Rounded to slightly elongated in suture plane. Average depth 5.0 mm. Average diameter 5.2 mm.

Stem:

*Size.*—Small. Average length 6.7 mm. Average diameter 3.4 mm.

*Color.*—Varies from 2.5GY 5/8 to 5GY 5/8.

Flesh:

*Ripens.*—Evenly.

*Texture.*—Firm, meaty.

*Fibers.*—Few, small, tender.

*Firmness.*—Good, comparable to other commercial apricot varieties.

*Aroma.*—Slight.

*Amydgalin.*—Undetected.

*Eating quality.*—Very good.

*Flavor.*—Very good. Good balance between acid and sugar.

*Juice.*—Moderate amount, enhances flavor.

*Acidity.*—Not available.

*Brix.*—Average Brix 17.0°, varies slightly with amount of fruit per tree and climatic conditions.

*Pit cavity.*—Average length 26.0 mm. Average width 24.7 mm. Average depth 8.8 mm. Color varies from 5YR 7/10 to 5YR 6/10

*Color.*—Varies from 5YR 6/12 to 7.5YR 7/10. .

Skin:

*Thickness.*—Medium.

*Surface.*—Smooth to slightly waffled.

*Pubescence.*—Finely pubescent.

*Tendency to crack.*—None.

*Color.*—Ground color varies from 5YR 7/10 to 7.5YR 7/10. Partially overspread with 7.5R 5/8 to 7.5R 5/10.

*Tenacity.*—Tenacious to flesh.

*Astringency.*—Undetected.

Stone:

*Type.*—Freestone, weak adherence.

*Size.*—Large. Average length 24.6 mm. Average width 20.5 mm. Average thickness 13.5 mm.

*Form.*—Ovoid.

*Base.*—Flat.

*Apex.*—Rounded.

*Surface.*—Slightly pitted throughout, a shallow groove on each side extending from base to apex.

*Sides.*—Unequal, one side extending further from the suture plane.

*Ridges.*—Relatively smooth, extending from base to apex.

*Tendency to split.*—None.

*Color.*—Varies from 7.5YR 3/2 to 7.5YR 3/4 when dry.

Kernel:

*Size.*—Large. Average length 18.6 mm. Average width 13.5 mm. Average depth 8.2 mm.

*Form.*—Ovoid.

*Viability.*—Viable, complete embryo development.

*Skin color.*—Varies from 5Y 9/2 to 5Y 8.5/2.

Use: Dessert.

*Market.*—Local and long distance.

Keeping quality: Good, held firm in cold storage for 3 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

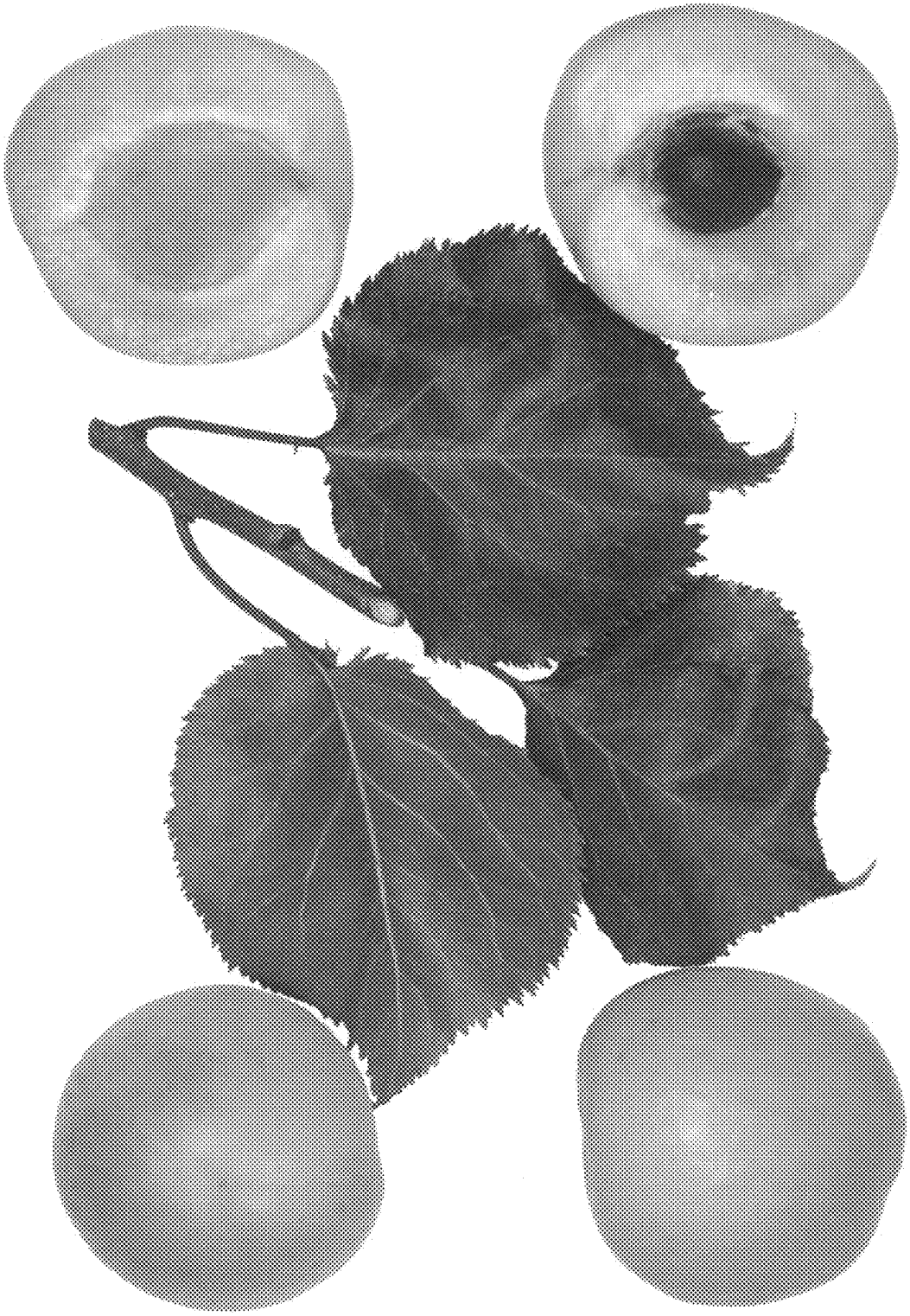

* * * * *